United States Patent
Newman et al.

(10) Patent No.: US 10,383,715 B2
(45) Date of Patent: Aug. 20, 2019

(54) TRANSDERMALLY POWERED ELECTRIC PUMP IN RESERVOIR INFLATOR FOR INFLATABLE MEDICAL IMPLANTS

(71) Applicants: Howard S. Newman, Annapolis, MD (US); Marcel I. Horowitz, Baltimore, MD (US)

(72) Inventors: Howard S. Newman, Annapolis, MD (US); Marcel I. Horowitz, Baltimore, MD (US)

(73) Assignee: MHN BIOTECH LLC, Baltimore, MD (US)

( * ) Notice: Subject to any disclaimer, the term of this patent is extended or adjusted under 35 U.S.C. 154(b) by 602 days.

(21) Appl. No.: 15/153,382

(22) Filed: May 12, 2016

(65) Prior Publication Data
US 2017/0079760 A1    Mar. 23, 2017

Related U.S. Application Data

(60) Provisional application No. 62/220,593, filed on Sep. 18, 2015.

(51) Int. Cl.
*A61F 2/00* (2006.01)
*A61F 2/26* (2006.01)

(52) U.S. Cl.
CPC .............. *A61F 2/004* (2013.01); *A61F 2/26* (2013.01); *A61F 2250/0002* (2013.01); *A61F 2250/0003* (2013.01)

(58) Field of Classification Search
CPC ........... A61F 5/005; A61F 5/0053; A61F 2/04
USPC .............................................. 600/29–31, 37
See application file for complete search history.

(56) References Cited

U.S. PATENT DOCUMENTS

| | | | |
|---|---|---|---|
| 4,441,491 A | 4/1984 | Evans, Sr. | |
| 4,781,525 A | 11/1988 | Hubbard et al. | |
| 5,016,720 A | 5/1991 | Coker | |
| 6,482,145 B1 * | 11/2002 | Forsell | A61F 2/0018 600/30 |
| 8,545,384 B2 | 10/2013 | Forsell | |
| 8,545,393 B2 | 10/2013 | Ellering | |
| 8,585,580 B2 | 11/2013 | Vaingast et al. | |
| 8,678,997 B2 | 3/2014 | Forsell | |
| 9,050,165 B2 * | 6/2015 | Perron | A61F 5/0059 |
| 2013/0190559 A1 | 7/2013 | Little | |
| 2015/0374906 A1 * | 12/2015 | Forsell | A61M 1/127 600/31 |

OTHER PUBLICATIONS

International Search Report dated Aug. 18, 2016, corresponding to International Application No. PCT/US2016/032154.

* cited by examiner

*Primary Examiner* — Samuel G Gilbert
(74) *Attorney, Agent, or Firm* — Hogan Lovells US LLP

(57) ABSTRACT

A wirelessly controlled inflatable medical implant system includes an external control module and an implantable module. The external control module may transmit wireless power and control signals, which are received by circuitry on a flexible printed circuit board in the implantable module. In response to the received signals, circuitry in the flexible printed circuit board may cause a motor and pump combination to transfer fluid from a reservoir in the implantable device, through tubing, and into inflatable medical implant located in the penis. The flexible printed circuit board, motor, and pump may be placed within the fluid reservoir, which provides a heat sink that prevents overheating of the implant.

18 Claims, 7 Drawing Sheets

501 Stator Winding

502 Rotor Bars

503 Molded Stator

504 Molded Rotor

TRANSDERMALLY POWERED ELECTRIC PUMP IN RESERVOIR INFLATOR FOR INFLATABLE MEDICAL IMPLANTS

CROSS REFERENCE TO RELATED APPLICATIONS

This application claims priority to U.S. Provisional Application No. 62/220,593 filed on Sep. 18, 2015. The entire disclosure of the prior application is hereby incorporated by reference herein.

FIELD OF THE INVENTION

The present invention is directed to an apparatus and method for treating erectile dysfunction, urinary and fecal incontinence, and other medical problems treated with inflatable medical implants. In particular, the apparatus includes a software application for setting and monitoring apparatus use parameters; an external controller which includes a power source, electronics for transdermal power transmission, display, control and communications and patient displays and controls. Specifically, the invention provides for transdermally controlled and powered implants including an isotonic fluid reservoir containing transdermal power reception circuitry, a flex circuit board housing integrated circuits and one or more rotary electric pumps that inflate and deflate one or more inflatable medical implants.

BACKGROUND OF THE INVENTION

Existing erectile dysfunction implants typically use manually operated pumps and reversing switches implanted in the scrotum to transfer fluid back and forth between inflatable cylinders implanted in the penis and a fluid reservoir implanted in the abdomen. Some patients, particularly older people with arthritis, find it difficult to operate the pump and switch, and, therefore, may elect not to have the implant.

Existing artificial urinary and anal sphincters implants use continuous passive pressure from a fluid reservoir implanted in the abdomen to inflate cuffs implanted around the urethra or anus. To operate, the patient depressurizes the cuff by manually depressing a pump, implanted in the scrotum for men and the labia for women, to transfer fluid from the cuff back to the reservoir. The cuff then repressurizes automatically to achieve continence. Like the penile implant, manual pump operation may be difficult, especially for women, where the pump's location makes operation difficult, may cause chronic discomfort and may limit activities such as bicycle riding.

Additionally, current artificial sphincter lifespans may be limited by tissue atrophy. This common complication is likely caused by cuff dynamics, where constant pressure is applied to the biological structure over long time periods, and may be worsened by tissue frailty due to aging and cancer radiation treatments.

More recent implant concepts may replace the manual pump with an electrically driven pump and reversing switches which may be controlled and powered from an external source. In operation, an external unit may send wireless control signals to an internal unit, which then activates the pump. In certain systems, the internal control unit and pump are powered by an internal source, such as batteries. In others, external power may be transmitted transdermally by close-coupled magnetic induction, which forms an air core electrical transformer.

A recent erectile dysfunction implant concept replaces the manual pump with a transdermal close-coupled magnetic induction powered solenoid driven pump, analogous to a powered hypodermic syringe, to provide inflation and deflation. However, these devices may be limited because the solenoid pump implant is much larger than the manual pump implant's reservoir, as the solenoid must move out from the reservoir by as much as it moves in. Additionally, these devices may be MRI-unsafe because the solenoid's iron core may translate and rotate from MRI's magnetic fields, and may heat from the MRI's radio frequency (RF) field.

Another recent implant concept for erectile dysfunction and urinary and fecal incontinence replaces the manual pump with an electric motor and pump or a nonmagnetic piezoelectric motor powered transdermally by close-coupled magnetic induction and external to internal control signals. These devices are limited because under leak conditions, the motor will run continuously until power is exhausted and the piezoelectric motor may produce limited pumping force at single digit efficiency resulting in slow operation and excess heating. Additionally, the coupling of the piezoelectric motor to the pump, complicated motor drive electronics and the use of powered valves may be volume intensive, of lower reliability and MRI-unsafe.

Furthermore, these devices transmit power transdermally by close coupled magnetic induction, which forms an air core electrical transformer with its primary winding external to the patient and its secondary winding internal to the patient. Due to the low permeability of air and body tissue, magnetic flux linkages between these primary and secondary windings are not concentrated like they are in an iron core transformer. Therefore the implanted transformer secondary must be implanted in the dermis, a millimeter from the transformer's external primary placed over the skin, a physically and cosmetically uncomfortable situation. Additionally, the amount of transdermal power that can be safely transferred is limited due to heating caused by the primary winding's strong electric field, which results from needing to magnetically transmit power through air and tissue.

Also, physician changing of preset inflatable implant pressures is an invasive procedure; they offer no implant performance monitoring by the patient or physician; they have no means of relieving cylinder or cuff pressure should the implant fail; they address only one dysfunction at a time; and they do not allow for implant performance analysis across many patients.

What is needed is a compact, easy to operate apparatus that is programmable, MRI-conditional and can treat multiple dysfunctions with one implant. A device is needed that can transmit sufficient power and bidirectional communications signals over longer distances, relieve cylinder and cuff pressure upon implant failure, not invade the labia or scrotum, increase artificial sphincter lifespan, and allow analysis of data across patients.

SUMMARY OF THE INVENTION

The present invention is directed to an apparatus and method for treating erectile dysfunction, urinary and fecal incontinence, and other medical problems treated with inflatable medical implants. The apparatus includes a Physician's Software Application, an External Controller, an implantable module including a Pump in Reservoir Implant, and an Inflatable Medical Implant. The physician may use the Physician's Software Application, executed on a computational device, to set, monitor and noninvasively change implant inflation parameters stored in the External Controller. It may also collect controller data from the physician's patients so trends in performance may be analyzed for determining settings and for scientific papers. Communications between the Physician's Software Application and the External Controller may be hardwired, such as USB, or wireless, such as Bluetooth, Wi-Fi or NFC.

Once the External Controller is programmed by the physician, the patient may use pushbuttons and a touch screen to send power, control signals and settings transdermally to the Pump in Reservoir Implant to inflate or deflate one or more Inflatable Medical Implants. The External Controller may also be programmed to alleviate tissue atrophy due to constant cuff pressure by lowering cuff pressure at night when less pressure is needed in supine patients to achieve continence.

The External Controller may operate with the Pump in Reservoir Implant using resonant wireless power technology transmission and bidirectional data transfer. A battery charging station, included with the External Controller, may provide direct current (DC) power to recharge the External Controller's rechargeable battery power source. The charging station may run on 110-220V, 50-60 Hz and 12V automobile battery power.

Upon receiving a control signal and data from the External Controller, a MRI-conditional Pump in Reservoir Implant, located in the abdomen, may inflate or deflate one or more Inflatable Medical Implants. During use, it may send performance data, such as pressure readings, back to the External Controller for patient viewing and for storage for later analysis by the physician using the Physician's Software Application.

The Pump in Reservoir Implant may contain isotonic fluid, electronics and multiple electrically driven pumps to inflate and deflate implants, such as penile cylinders or artificial urethra or sphincter cuffs, to treat erectile dysfunction in men, urinary and fecal incontinence in both men and women and other conditions. Upon reception of a control signal and power from the External Controller, the pumps may transfer isotonic fluid to and from the reservoir and one or more Inflatable Medical Implants for inflation and deflation. The amount of fluid transferred may be controlled by powering the pumps for a fixed number of rotations.

The pumps may be operated by rotary electric motors, such as nonferrous 3-phase squirrel cage or synchronous motors. The motor' power may be received transdermally from the External Controller via resonant power transfer. A resonant power receiver in the Pump in Reservoir Implant may receive and convert the transmitted power into stable DC power for use by a microprocessor and power amplifiers. The microprocessor may then generate a 3-phase signal and triple power amplifiers may then provide the 3-phase power to drive the motors. No power is stored internally in the Pump in Reservoir Implant.

Pump in Reservoir Implant sensors may then monitor pumping operation for failures such as out of range pump speed, leaks, electrical shorts and high temperatures. Sensor data may include reservoir and Inflatable Medical Device pressure, pump speed, motor current and voltage and reservoir temperature. These data may also be sent back the External Controller for monitoring by the patient and for storage for later analysis by the physician. The physician may then noninvasively change inflation parameters by reprogramming the External Controller.

The electronic components may be house on a coated, flexible printed circuit board. The flexible printed circuit board, electric motor and pump may be submerged within the fluid reservoir to provide a heat sink that prevents local overheating of the patient during operation and during MRI examination.

One or more independently controlled pumps may be placed in the reservoir to treat multiple dysfunctions. The Pump in Reservoir Implant may be made from MRI-conditional material, such as a nonferrous electronics, motors and pumps. The implant may also be made with components that contain ferrous materials making it MRI-unsafe.

DETAILED DESCRIPTION OF THE INVENTION

Figure 1:
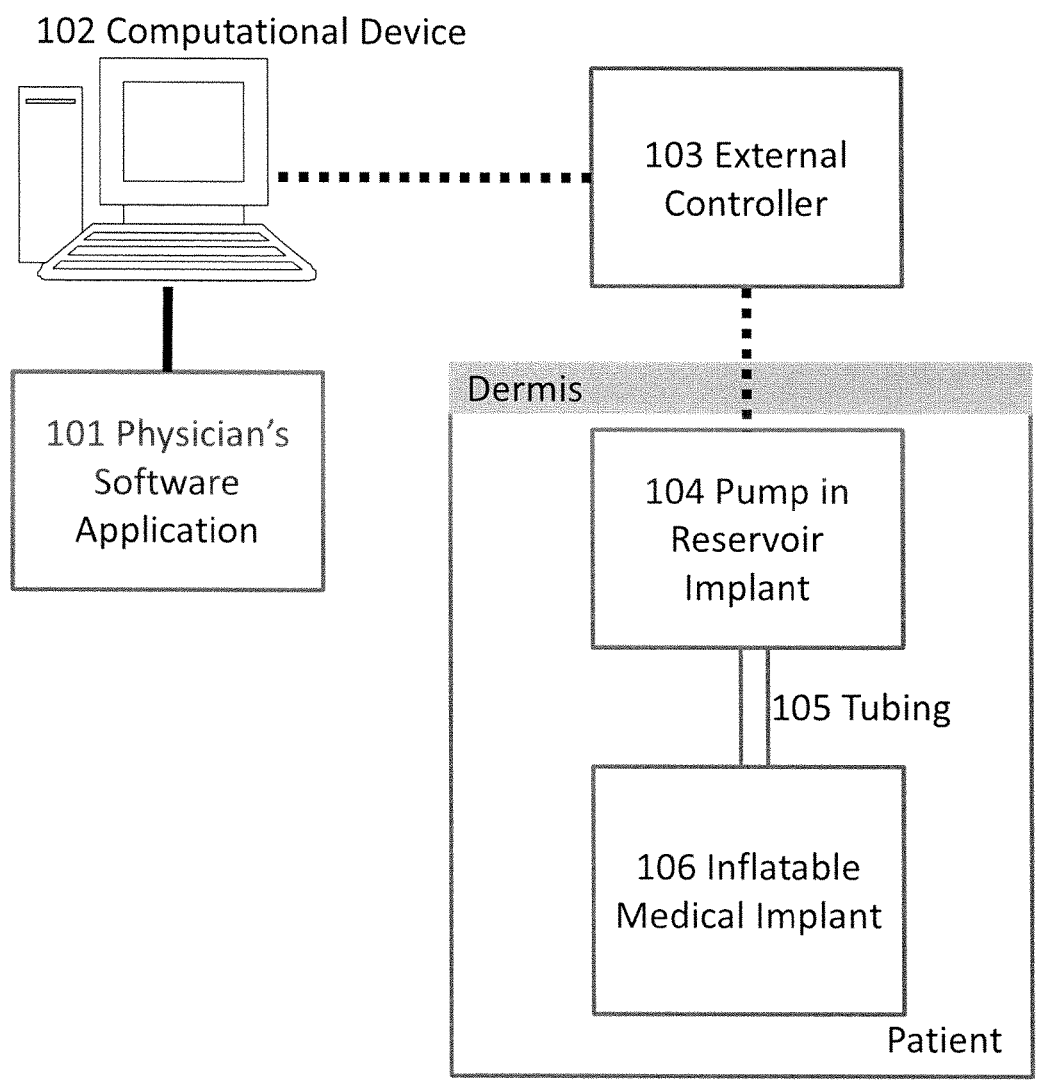
FIG. 1 is a diagram illustrating the invention's components.

The present invention is directed to an apparatus and method for treating erectile dysfunction, urinary and fecal incontinence and other conditions treated by inflatable medical implants. As shown in FIG. 1, the apparatus includes a Physician's Software Application 101 which can run on computational devices 102, and which allows the physician to program an External Controller 103 for use by patients.

The patient, using the External Controller 103, may then operate a Pump in Reservoir Implant 104 to inflate and deflate an Inflatable Medical Implant 106. Sensors in the Pump in Reservoir Implant 104 report performance data for fault detection and back to the External Controller 103 for additional fault detection, viewing by the patient and for storage for later transmission to the Physician's Software Application 101 for use by the physician to noninvasively change inflation parameters and for statistical analysis across patients.

The Physician's Software Application 101, executed on a computing device 102, such as a laptop, desktop, smartphone, or tablet, may allow the physician to set, monitor and noninvasively change implant inflation parameters stored in the External Controller 103 and then send them to the Pump in Reservoir Implant 104. Inflation parameters may include number of pump revolutions, pump speed versus time and safety limits such as pressure and temperature. It may also collect data from multiple patients so trends in usage and performance may be analyzed for determining settings and for scientific papers.

External Controller's 103 inflation data may originate from the physician, the apparatus provider and from apparatus performance data it receives from sensors placed in the apparatus, which may be stored in the External Controller 103 during each usage for later transmission to the application. When in range, such as during office visits or hospitalizations, the Physician's Software Application may transfer computer programs and data to the External Controller 103 using encrypted transmissions via wired and wireless channels such as USB, Bluetooth, Wi-Fi or NFC. These channels may also be used for the performance data stored in the External Controller 103. All software may be updated from time to time by the apparatus provider over the internet A Pump in Reservoir Implant 104 is provided that receives power, control signals and data from the External Controller 103, on command pumps isotonic fluid to inflate and deflate Inflatable Medical Implants 106, and returns performance data to the patient and physician via the External Controller 103 and the Physician's Software Application 101. The Pump in Reservoir Implant 104 may be inserted into the patient's abdomen and connected to the Inflatable Medical Implant 106 via Tubing 105 during a single surgery. It may contain more than one pump to treat multiple conditions.

Figure 2:
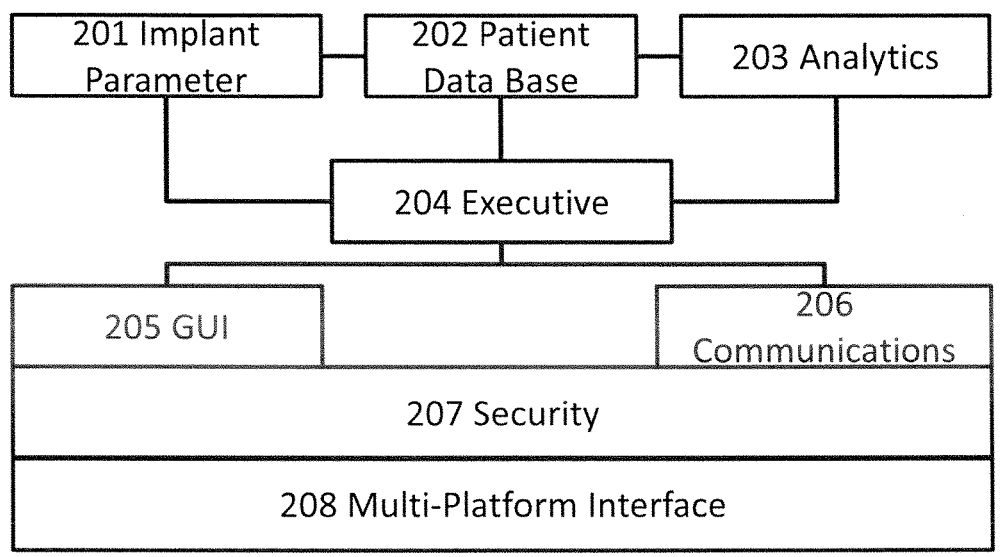
FIG. 2 is a bock diagram of the Physician's Software Application.

A block diagram of the software modules contained in the Physician's Software Application is shown in FIG. 2. The Implant Parameter module 201 may provide the physician with the capability to update External Controller 103 software, set inflation parameters and monitor operation of the implant. The physician may set the amount of fluid that the pump transfers at what speed for each operation during each time of day. For example, to increase artificial sphincters life, the physician may want to find the minimum amount of fluid to transfer, day and night, to achieve continence. Pump operating time and output pressure data may then be used to assist the physician in finding this minimum, and noninvasively adjust it over time, as tissue atrophies.

Data from the Implant Parameter module 201 may be stored in an encrypted Patient Data Base module 202. The Patient Data Base module 202 may store all the physician's implant patient data. An Analytics module 203 may provide the physician with the capability to study trends in patient data contained in the Patient Data Base 202. Analysis may include looking at atrophy rates of artificial sphincter patients with specific devices, determining when a particular patient's cuff is about to fail, and warning of pumps and motors that are about to fail. An Executive module 204 may control and oversee the use of other modules by providing services such as such a logon, logoff and module selection. A Graphic User Interface, GUI, module 205 may provide the displays and controls for the physician to interface with the application's modules. A Communications module 206 may provide data transfer between the Implant Parameter module 201 and the External Controller 103. A Security module 207 may provide data encryption and physician authentication. And, a Multi-Platform Interface 208 may provide application operation across different physician platforms with different screen sizes.

An External Controller 103 is provided that interacts with and controls the Pump in Reservoir Implant 104. The External Controller 103 may send power to the Pump in Reservoir Implant 104, and may send data to and receive data from the Pump in Reservoir Implant 104, thus allowing a patient to transdermally activate, control and power the Pump in Reservoir Implant 104.

On command from the patient, the External Controller 103 may wirelessly send control signals, power and inflation parameters to the Pump in Reservoir Implant 104 for its operation. It may receive reservoir and pump pressure data, pump speed, motor current and voltage, reservoir temperature, or usage data from the Pump in Reservoir Implant 104. Power transmission may be by AirFuel" or "Qi" compliant standards and communication may be by "AirFuel" or "Qi" compliant, Bluetooth or Wi-Fi standards.

Figure 3A:
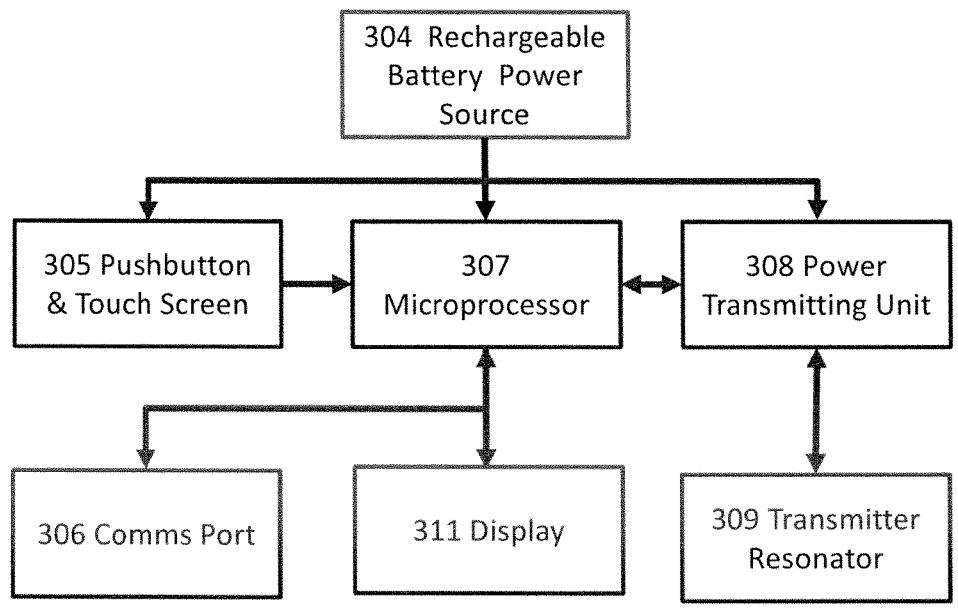
FIG. 3A is a block diagram representation of the components of the External Controller.
Figure 3B:
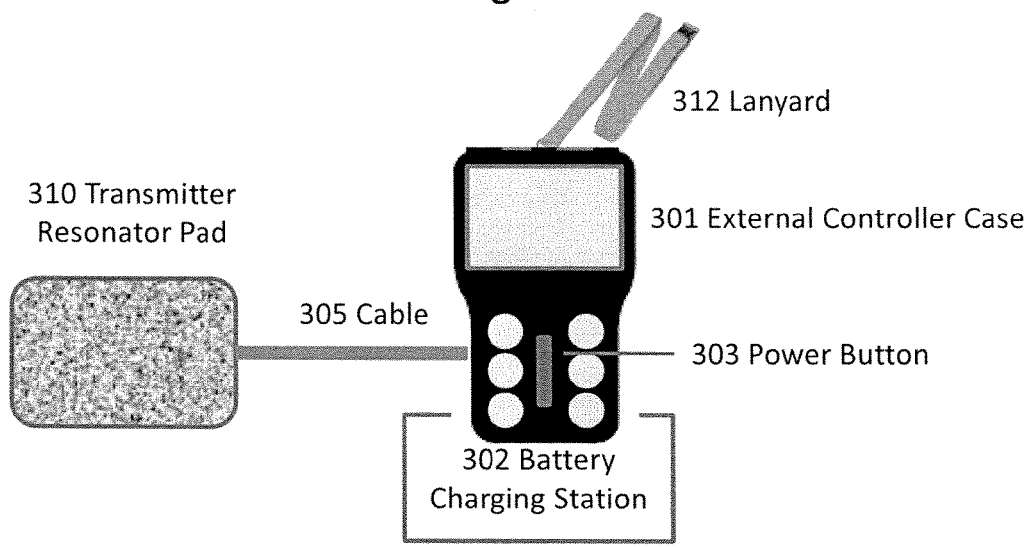
FIG. 3B is an illustration of an example External Controller.

FIG. 3A is a block diagram representation of the components of the External Controller, and FIG. 3B shows an illustration of an example External Controller. When not in use, the External Controller 301 may sit in a Battery Charging Station 302. The station may provide DC power to charge the External Controller's rechargeable batteries 304. Overcurrent, short circuit and over temperature protection may be provided. The Battery Charging Station 302 may be powered from 110-220 V, 50-60 Hz or 12 VDC car battery sources. When a Power Button 303 is pressed, the Rechargeable Battery Power Source 304 may supply power to the External Controller to wake up its functions and await commands from the patient via patient controls 305 or from the physician via a Communications Port 306. The External Controller's Rechargeable Battery Power Source 304 may include a rechargeable battery such as Lithium Ion or NiMH.

Patient controls 305 may be provided via push buttons, a touch screen or both. They may include "On, Off, Inflate and Deflate." Multiple controls may be provided for implants operating more than one Inflatable Medical Device 106. Upon activating any control, an interrupt may be sent to a Microprocessor 307 which contains a nonvolatile memory storing an executable computer program, physician's settings, such as number of urinary cuff motor rotations for day and for night use, and implant usage data. A software interrupt service routine then determines which control was activated and what action to take. Should the action require operation of the Pump in Reservoir Implant 104, control signals and the appropriate data, such as pump rotations, are sent to the Power transmitting Unit 308 over a data bus, such as an $I^2C$ serial interface.

The Microprocessor 307 may be programmed through the Physician's Software Application 101 located on the physician's computational device 102. The Microprocessor 307 may be programmed to stop operation if the signal is lost or preset safety parameters, such as pressure, pump speed range, motor current and voltage and temperature are exceeded. The Microprocessor 307 may turn off power if no activation signals are received after a preset time interval. Upon reception of a control signal and data from the Microprocessor 307, a Power Transmitting Unit, PTU, 308 may generate and transmit power and data transdermally via a Transmitting Resonator 309 to the Pump in Reservoir Implant 104, and may operate at the 6.78 MHz "AirFuel Alliance" resonance specified frequency, a decade below the 63.87 MHz RF transmitter frequency of 1.5-tesla MRI machines.

Additionally, encrypted control signals and data may be sent to the Pump in Reservoir Implant 104 wirelessly via Bluetooth, Wi-Fi or NFC. Also, the wireless communications, along with the Communications Port 306, may be used to communicate with the Physician's Software Application 101.

The Transmitter Resonator 309 may include a coiled wire inductor and a series capacitor whose combination may resonate at 6.78 MHz. A wire coil may be located in both the External Controller Case 301 and in the Transmitter Resonator Pad 310, which may be provided to make it easy for the patient hold the wire coil on the skin over the implant. The pad and the case are connected via a plugin Cable 305. Plugging the Cable 305 into the case 301 may disconnect the case's coil. For operation, the patient may place the case 301 or the pad 310 on the skin over the Pump in Reservoir Implant 104, and then operate the desired control 305. Resonant technology may be used to transmit power because it produces an evanescent electromagnetic field, as opposed to a close-coupled magnetic field, for longer distance, higher power operation. The Transmitter Resonator 309 may transmit power to the implant with up to 1-inch separation between the resonator's wire coil and the implant. Other resonant power technologies, such as Wireless Power Consortium "Qi" compliant devices, may also be used.

Performance and safety data from the Pump in Reservoir Implant 104 may be sent back to a Display 311 via the Transmitter Resonator 309, the Power Transmitting Unit 308 and the Microprocessor 307 for viewing by the patient and physician. It may also be recorded in the Microprocessor 307 for later use by the physician. In particular, time-varying reservoir and Inflatable Medical Device 106 pressure, pump speed, motor current and voltage and reservoir temperature may be received.

FIG. 3B provides an illustration of an Example External Controller. As shown, the External Controller may include a case 301 with a touch screen and control buttons. The buttons are set to provide On and Off control of three pumps in one implant. The center button 303 is a Power On and Off button. For an implant with only one motor, three buttons may be provided. The External Controller may also have a lanyard 312 which may allow patients to hang the controller from the neck while in use, such as between starting and stopping urination or defecation.

Figure 4A:
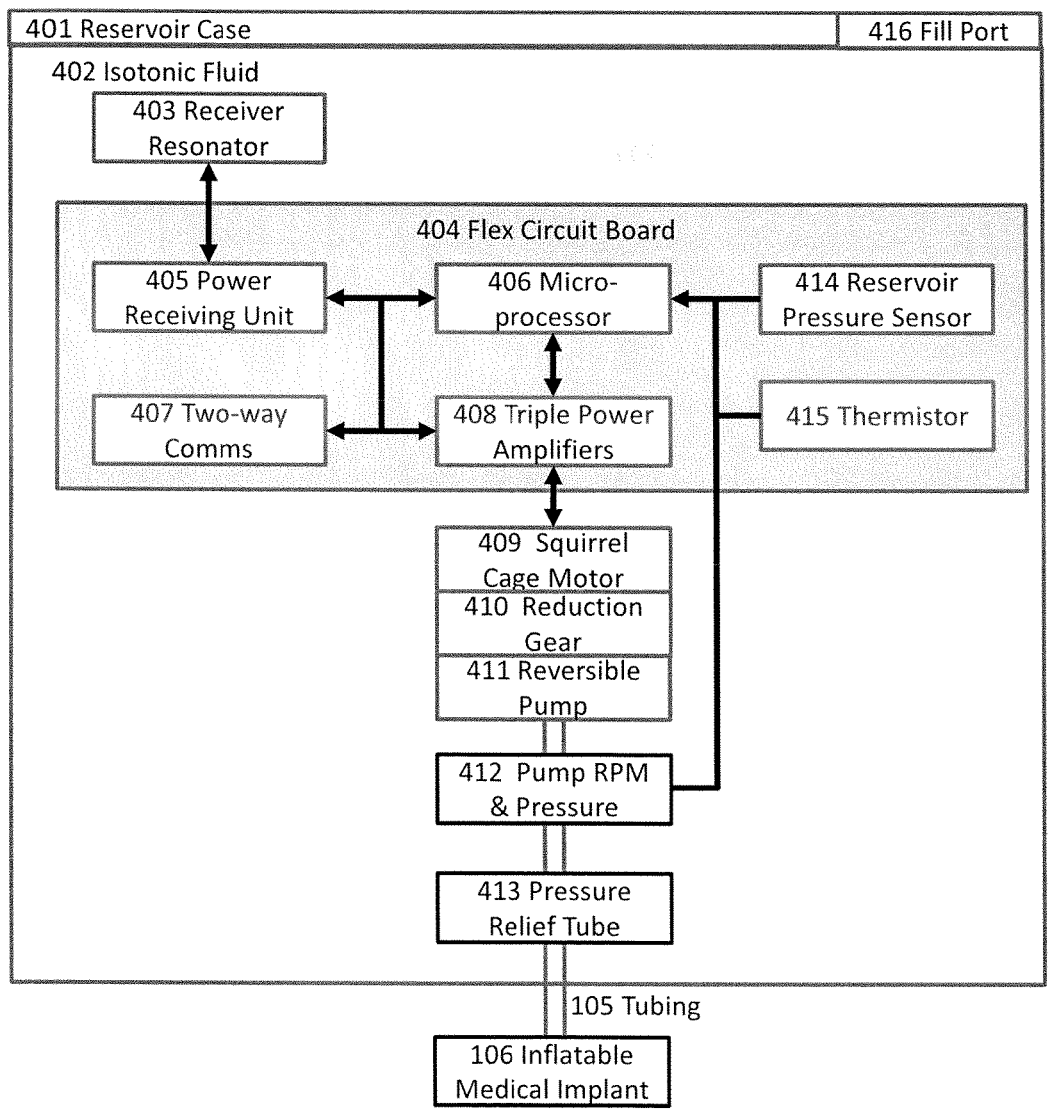
FIG. 4A shows a diagram of the MRI-conditional Pump in Reservoir Implant operating a single Inflatable Medical Implant.
Figure 4B:
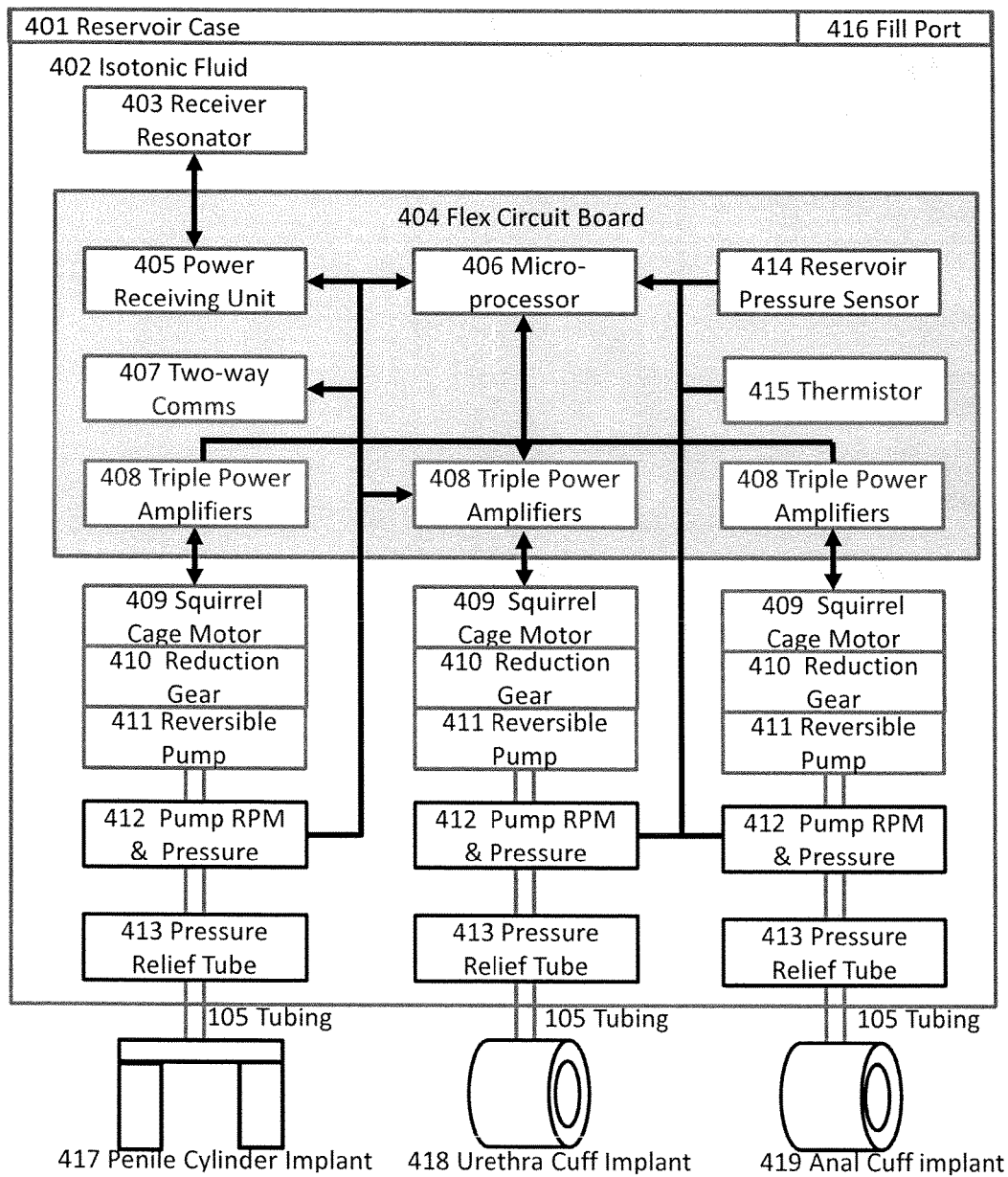
FIG. 4B shows a diagram the MRI-conditional Pump in Reservoir Implant operating three Inflatable Medical Implants.

Details of the Pump in Reservoir Implant 104 operating a single Inflatable Medical Implant 106 are shown in FIG. 4A. FIG. 4B shows a Pump in Reservoir Implant 104 operating three Inflatable Medical Implants 417, 418, and 419. The Pump in Reservoir Implant may be MRI-conditional, with components that would not cause problems when introduced into an MRI machine. The implant may also be implemented with components, FIG. 6, which may contain MRI-unsafe materials.

Figure 6:
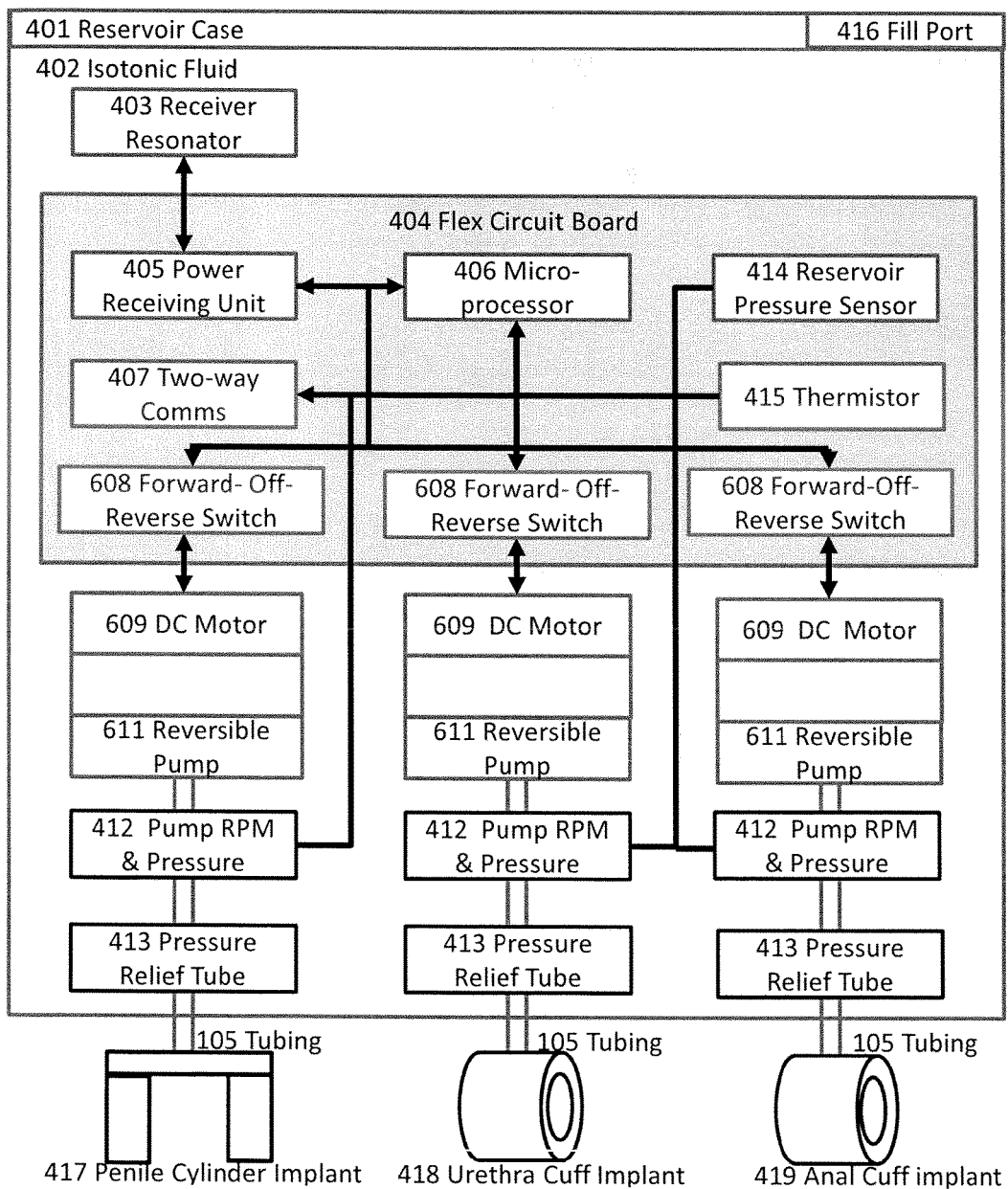
FIG. 6 shows the MRI-unsafe Pump in Reservoir Implant operating three Inflatable Medical Implants

As shown in FIGS. 4A, 4B and 6, both implementations may power any combination of penile cylinders, urinary and anal cuffs, and other inflatable medical implants. Since cuffs require less than $\frac{1}{10}^{th}$ the amount of fluid transfer than the cylinders, smaller combinations of pumps and reservoirs may be used for cuff only applications. In the MRI-conditional implementation, FIGS. 4A and 4B, the electronics, motors and pumps may be made from materials that do not contain ferrous materials (magnetic field pull and torque) or long electrical conductors (RF field heating).

In FIG. 4A, a Reservoir Case 401 may contain a transdermal power Receiver Resonator 403, nonferrous integrated circuits mounted on a flex circuit board, a nonferrous 3-Phase Squirrel Cage Motor 409, a Planetary Reduction Gear 410 and a Reversible Pump 411 all submerged in an Isotonic Fluid 402, such as normal saline solution. The isotonic fluid may be the operating fluid, provide a heat sink for the electronics, motor and pump, and not change the patient's local electrolytic balance should leakage occur. The Reservoir Case 401 may also have a biologically inert outer wall with an insulating material, such as Nomex, molded into the wall to reduce heat transfer rate from the isotonic fluid to the patient in this low duty cycle application. The empty reservoir may be folded into a cylindrical shape to ease insertion by the surgeon. The surgeon may then fill the Reservoir Case 401 with the Isotonic Fluid 402 through a Fill Port 416 after inserting it into the patient's abdomen. The Receive Resonator 403 may receive RF energy transdermally from the Transmitting Resonator 309. Additionally, it may be used as the antenna for bidirectional communication with the External Controller 103.

The Receive Resonator 403 may include a resonant circuit made up of a wire coil inductor and series capacitor, which may resonate at 6.78 MHz, and an electromagnetic interference, EMI, filtered bridge rectifier to convert the transdermally received RF power to DC. The wire coil may be molded into the Reservoir Case 401. The Receive Resonator 403 may also receive transdermal communication from the External Controller 103 and send it to a Power Receiving Unit, PRU, 405 for processing.

Implant electronics may be housed on a military-grade coated Flex Circuit Board 404 for protection and waterproofing. Flexible circuit board packaging may facilitate Reservoir Case 401 implantation by the surgeon. The circuit board may be molded into the Reservoir Case 401 wall along with the Receive Resonator Filter 403 or wrapped around the motor and pump and coated with waterproof plastic. This package may be suspended in the center of the Reservoir Case 401. The board and its components may be MRI-conditional.

The PRU, 405 may convert the widely varying DC output of the Receiver Resonator 403 to a constant voltage DC output. Receiver Resonator's wide voltage variance may be caused by differences in separation over time and patients between the Transmitting Resonator 309 and the Receiving Resonator 403.

The PRU 405 may provide power to a Microprocessor 406 and Triple Power Amplifiers 408. It may also process bidirectional communications from Receive Resonator 403. Signals sent from the External Controller 103 are fed to the Microprocessor 406 and data from the Microprocessor 406 are sent to the Receiver Resonator 403 for transmission to the External Controller 103.

Upon reception of a start signal, the Microprocessor 406, such as a MSP430 series or ADuCM320, may generate and digital-to-analog convert three sinusoids set 120° apart. The sinusoidal frequency and the number of sinusoidal cycles to be generated may be set from the Physician's Software Application 101. The physician may select the number of cycles generated to set the number of rotary pump revolutions, and, for a fixed displacement pump, the amount of fluid transferred to inflate and deflate the cylinders and cuffs. Pump operation may also be set by using pressure data from the Pump Pressure and revolutions per minute, RPM, sensor 412; however, counting pump revolutions may be safer as it limits the amount of fluid transferred under leakage conditions.

Switching between inflation and deflation may be achieved by switching two phases of the three 3-phase signals, which reverses motor direction. The Microprocessor 406 may also receive, process, and format implant performance and safety data for transmission to the External Controller 103. In some implementations, additional analog-to-digital and digital-to-analog integrated circuit chips may be included.

The 3-phase signals generated by the Microprocessor 406 may then feed Triple Power Amplifiers 408, which then generate the power to operate the 3-Phase Squirrel Cage Motors 409 or synchronous motors. Current and voltage at the Triple Power Amplifiers 408 may be monitored by the Microprocessor 406 to detect faults for safe operation.

This apparatus may include a nonferrous, 3-phase, 4-pole squirrel cage motors 409 or a synchronous motor to drive a Reduction Gear 410 and a Reversible Pump 411. A 3-phase squirrel cage or synchronous motor has the advantages of small size, self-starting, high frequency operation. Squirrel cage motors do not use brushes or slip rings, wear items which may reduce motor life.

The starting basis for the apparatus, and therefore motor and pump selection, is size, the amount of fluid that must be pumped to inflate the Inflatable Medical Implant 106 and patient convenience including the time it takes to inflate and deflate the implant. These parameters are physician set at the beginning of the apparatus design process. Water pumping equations are then used to determine how much power is required at the pump output, and, accounting for pump efficiency, how much power is required at the pump input. MRI-unsafe ferrous DC motor and pump combinations are widely available to meet these parameters.

But these motors use ferrous materials to greatly increase torque by concentrating magnetic flux linkages between the motor's stator and rotor. For a constant speed motor, removing ferrous materials for MRI safety reduces flux linkages thereby greatly reducing torque, and, therefore power output, which is proportional to shaft speed multiplied by torque. The apparatus shown in FIGS. 4A and 4B makes up for lost nonferrous motor torque by increasing motor speed as much as possible, thereby buying back some of the lost motor power. But pumps are not efficient at high speeds, so a Reduction Gear 410 is introduced to match the high speed, low torque motor to the lower speed, higher torque pump, thereby optimizing the combination's efficiency and size.

Figure 5A:
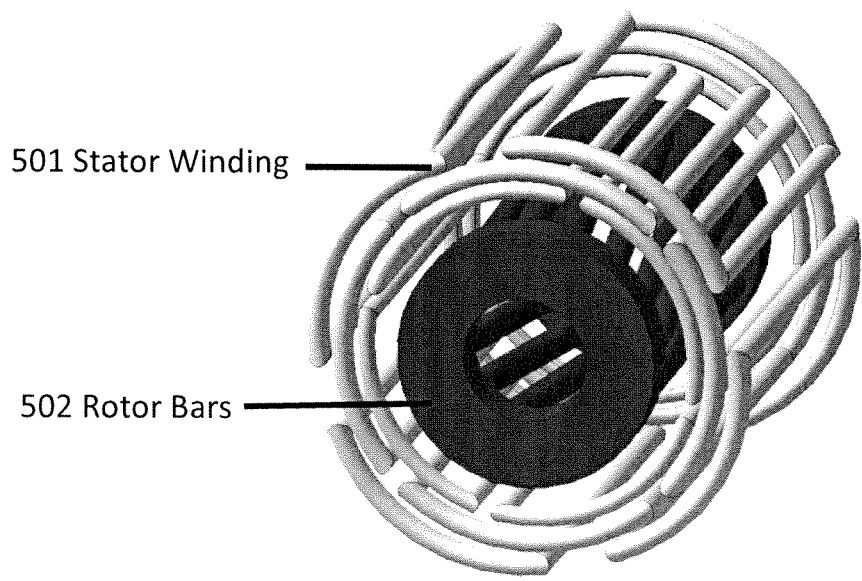
FIG. 5 shows diagrams of a nonferrous squirrel cage motor used in a finite element model.
Figure 5B:
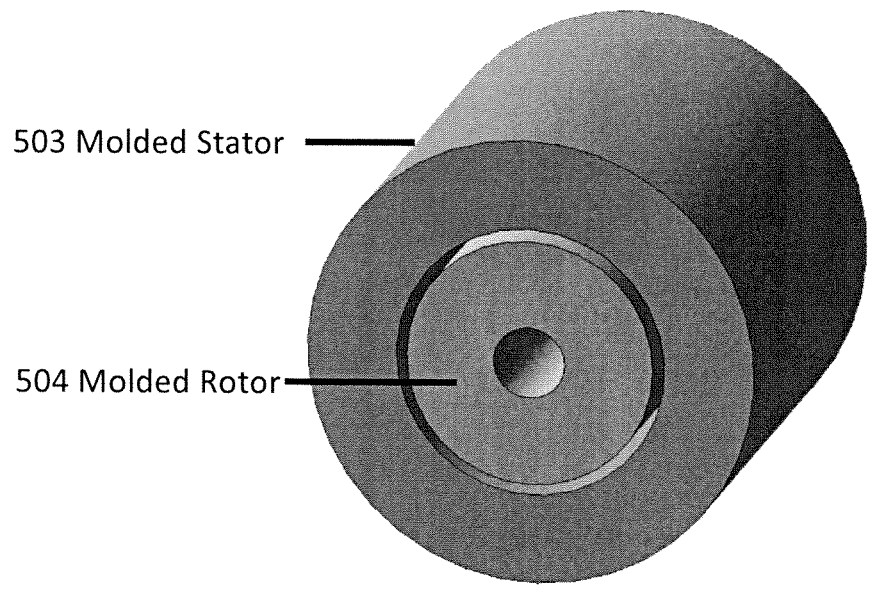

FIGS. 5A and 5B illustrate an example of a 20 mm diameter by 25 mm long, 3-phase 4-pole squirrel cage motor, supplied with 14.9 Vrms 2300 Hz power, and operating at 50,000-rpm. FIG. 5A shows the motor's 4-pole stator windings and interconnections 501 and the squirrel cage bars with short circuiting endplates 502. In FIG. 5B, the stator 503 and the rotor 504 have be encapsulated in molded plastic to reduce windage losses and to stabilize the Rotor 504 under centrifugal force. The nonferrous motor may drive a nonferrous 25:1 reduction gear and pump to adequately inflate the penile cylinders in good time. Cuffs require much less fluid transfer; therefore a much smaller motor without reduction gear may be used.

Therefore, as shown in FIG. 4A, the apparatus may include a nonferrous Squirrel Cage Motor 409 or a 3-phase synchronous motor, planetary Reduction Gear 410 and positive displacement Reversible Pump 411 to pump Isotonic Fluid 402 from the reservoir to the Inflatable Medical Implant 106.

Pump Pressure and RPM sensors 412 may be provided along with a reservoir Pressure Sensor 414. Pressure and RPM data may be sent to the Microprocessor 406. The pressure and RPM data may be used for automatic cutoff should the pump run over or under speed limits, leakage, over inflation or a fluid blockage occur and to help the physician set the amount of fluid to be transferred that is best for the patient.

A Thermistor 415 may be included on the Flexible Circuits Board 404 to send temperature data to the Microprocessor 406 for high temperature cutoff should the Isotonic Fluid 402 overheat. Additionally, integrated circuit chips used in the Power Receiving Unit 405, Microprocessor 406 and Triple Power Amplifiers 408 may have internal temperatures sensors that turn off the chip in over temperature situations.

Should the apparatus fail with the Inflatable Medical Implant 106 inflated, a Pressure Relief Tube 413 may be provided to allow physicians to manually deflate the Inflatable Medical Implant 106 by inserting a small bore hypodermic needle into the tube and drawing out the inflating fluid. One end of the tube may be located at the output of the Reversible Pump 412 and the other end just below the skin.

The Reversible Pump 413 may be connected to the Inflatable Medical Implant 106 through Tubing 105 which the surgeon threads from the Reservoir Case 401 to the Inflatable Medical Implant 106. At this time, the surgeon may fill the Implant Case 401 with Isotonic Fluid 402 through the Fill Port 416. Filling may be accomplished by inserting a hypodermic needle through the self-sealing Fill Port 416.

FIG. 4B shows the MRI-conditional apparatus operating three implants. The Figure shows a dual Penile Cylinder Implant 417, a Urethra Cuff Implant 418 and an Anal Cuff Implant 419 example.

FIG. 6 shows a diagram of the MRI-unsafe Pump in Reservoir Implant implementation. The implementation of FIG. 6 includes many of the same components already described in FIGS. 4A and 4B. However, in FIG. 6, the nonferrous pump and motor 409, 410, 411 from FIGS. 4A and 4B may be replaced by a reversible DC motor 609 and pump 611 combination. Reduction Gear 410 may not be needed. The coupling between the motor 609 and pump 611 may be magnetic allowing the pump to be in contact with the Isotonic Fluid 402 without the need for seals in the motor, thereby increasing efficiency and reliability. Also, the Triple Power Amplifier 408 may be replaced by connecting to the PRU's 405 DC output voltage through a Microprocessor 406 controlled solid state DC Forward-Reverse-Off Switch 608 to turn the motor on and off and to reverse its direction.

The invention claimed is:

1. A wirelessly controlled medical implant system, comprising:
    an external controller including selectable controls and wireless control circuitry;
    an implantable module in wireless communication with the external controller, wherein the implantable modules includes a fluid reservoir, flexible circuit board, at least one motor, at least one pump, pressure and rpm sensors, wherein the flexible circuit board, at least one motor and at least one pump are located within the fluid reservoir, and wherein the at least one pump and at least one motor are made of nonferrous materials; and
    at least one inflatable medical implant, connected to the fluid reservoir through flexible tubing, wherein the at least one inflatable medical implant is inflated by fluid transferred from the fluid reservoir through the tubing using the at least one pump.

2. The wirelessly controlled medical implant system of claim 1, wherein the external controller further includes a power transmitting module, and wherein the implantable module includes a power receiving module.

3. The wirelessly controlled medical implant system of claim 2, wherein the flexible circuit board includes circuitry to provide and control operation of the implantable module.

4. The wirelessly controlled medical implant system of claim 1, wherein an outer wall of the implantable module is biologically inert.

5. The wirelessly controlled medical implant system of claim 1, wherein the at least one pump includes a plurality of pumps, and the at least one inflatable medical implant includes a plurality of inflatable implants, each connected to a respective pump.

6. The wirelessly controlled medical implant system of claim 5, wherein the plurality of inflatable medical implants are selected from penile cylinders, urethra cuffs, and anal cuffs.

7. The wirelessly controlled medical implant system of claim 1, wherein the at least one motor includes a low torque 3-phase nonferrous squirrel cage or synchronous motor.

8. The wirelessly controlled medical implant system of claim 7, further comprising a reduction gear driven by the at least one motor.

9. The wirelessly controlled medical implant system of claim 1, wherein the at least one pump and at least one motor are a direct current motor and pump combination.

10. The wirelessly controlled medical implant system of claim 9, further comprising circuitry on the flexible circuit board configured to control a solid state forward-off-reversing switch.

11. The wirelessly controlled medical implant system of claim 1, further comprising a pressure relief tube.

12. The wirelessly controlled medical implant system of claim 1, wherein the at least one pump is a reversible pump.

13. The wirelessly controlled medical implant system of claim 1, wherein the external controller provides resonant transdermal power transfer with bidirectional data signals to the implantable module.

14. The wirelessly controlled medical implant system of claim 13, wherein the external controller and the implantable module are configured to provide a safety stop when the bidirectional data signals are lost or safety parameters are exceeded.

15. The wirelessly controlled medical implant system of claim 1, further comprising sensors configured to detect implant failure, pump speed range, leakage, short circuits, over pressure, and over temperature.

16. A method of wirelessly controlling an inflatable medical implant system, comprising:
    transmitting control signals from an external controller, wherein the external controller includes using wireless control circuitry;
    receiving the control signals at an implantable module, in wireless communication with the external controller, wherein the implantable modules includes a fluid reservoir, flexible circuit board, at least one motor, at least one pump, an pressure and rpm sensors, wherein the flexible circuit board, at least one motor and at least one pump are located within the fluid reservoir, and wherein the at least one pump and at least one motor are made of nonferrous materials; and
    activating the at least one motor and at least one pump in response to receiving the control signals to inflate at least one inflatable medical implant, connected to the fluid reservoir through flexible tubing.

17. The method of wirelessly controlling an inflatable medical implant system of claim 16, further comprising transmitting wireless power signals from the external controller, and receiving the wireless power signals with a power receiving unit in the implantable module.

18. A wirelessly controlled medical implant system, comprising:
    an external controller including selectable controls and wireless control circuitry;
    an implantable module in wireless communication with the external controller, wherein the implantable modules includes a fluid reservoir, flexible circuit board, at least one motor, at least one pump, pressure and rpm sensors, and wherein the flexible circuit board, at least one motor and at least one pump are located within the fluid reservoir;
    at least one inflatable medical implant, connected to the fluid reservoir through flexible tubing, wherein the at least one inflatable medical implant is inflated by fluid transferred from the fluid reservoir through the tubing using the at least one pump; and
    sensors configured to detect implant failure, pump speed range, leakage, short circuits, over pressure, and over temperature.

* * * * *